United States Patent
Walters et al.

(10) Patent No.: US 10,603,032 B2
(45) Date of Patent: Mar. 31, 2020

(54) LOCKING SPOOL HANDLE

(71) Applicant: Biomet Sports Medicine, LLC, Warsaw, IN (US)

(72) Inventors: Aaron Walters, Warsaw, IN (US); Joseph Whitley, Leesburg, IN (US)

(73) Assignee: Biomet Sports Medicine, LLC, Warsaw, IN (US)

(*) Notice: Subject to any disclaimer, the term of this patent is extended or adjusted under 35 U.S.C. 154(b) by 197 days.

(21) Appl. No.: 15/566,490

(22) PCT Filed: Apr. 22, 2016

(86) PCT No.: PCT/US2016/028956
§ 371 (c)(1),
(2) Date: Oct. 13, 2017

(87) PCT Pub. No.: WO2016/172559
PCT Pub. Date: Oct. 27, 2016

(65) Prior Publication Data
US 2018/0116659 A1 May 3, 2018

Related U.S. Application Data

(60) Provisional application No. 62/152,298, filed on Apr. 24, 2015.

(51) Int. Cl.
*A61B 17/06* (2006.01)
*A61B 17/04* (2006.01)

(52) U.S. Cl.
CPC .. *A61B 17/06061* (2013.01); *A61B 17/06123* (2013.01); *A61B 2017/0496* (2013.01)

(58) Field of Classification Search
CPC ........ A61B 17/06061; A61B 17/06114; A61B 17/06119; A61B 17/06123; A61B 17/06128; A61B 17/0491; A61B 17/0469; A61B 2017/06142
See application file for complete search history.

(56) References Cited

U.S. PATENT DOCUMENTS

| 2,550,927 A | 5/1951 | Jurnove et al. |
| 2003/0204193 A1 | 10/2003 | Gabriel et al. |
| 2012/0016384 A1* | 1/2012 | Wilke .............. A61B 17/06123 606/144 |

FOREIGN PATENT DOCUMENTS

| EP | 1852071 A2 | 11/2007 |
| WO | WO-9962808 A1 | 12/1999 |
| WO | WO-2016172559 A1 | 10/2016 |

OTHER PUBLICATIONS

"International Application Serial No. PCT/US2016/028956, International Search Report dated Jul. 8, 2016", 5 pgs.

(Continued)

*Primary Examiner* — Katherine M Rodjom
(74) *Attorney, Agent, or Firm* — Schwegman Lundberg & Woessner, P.A.

(57) ABSTRACT

An apparatus including a suture instrument including a handle and a post extending from the handle, the handle including a cavity; a cover slidably attached to the handle to cover the cavity; a post extending upward from a bottom surface of the cavity; and a suture spool removably positioned over the post; wherein the post includes a force member configured to provide upward force on the spool when the cover is slid off of the spool.

15 Claims, 2 Drawing Sheets

(56) References Cited

OTHER PUBLICATIONS

"International Application Serial No. PCT/US2016/028956, Written Opinion dated Jul. 8, 2016", 7 pgs.
"European Application Serial No. 16720976.6, Response filed Aug. 6, 2018 to Office Action dated Feb. 1, 2018", 12 pgs.
"European Application Serial No. 16720976.6, Comunication Persuant to Article 94(3) EPC dated Jul. 10, 2019", 1 pg.

* cited by examiner

LOCKING SPOOL HANDLE

CLAIM OF PRIORITY

This application is a U.S. National Stage Application under 35 U.S.C. 371 from International Application Serial No. PCT/US2016/028956, filed on Apr. 22, 2016, and published as WO 2016/172559 A1 on Oct. 27, 2016, which claims the benefit of priority of U.S. Provisional Patent Application Ser. No. 62/152,298, filed on Apr. 24, 2015, each of which are herein incorporated by reference in its entirety.

FIELD

The present subject matter relates to a suture aide and specifically to a locking spool handle.

BACKGROUND

Surgical procedures can be complex. For example, when applying a suture, a surgeon may desire to keep the suture from tangling, and to maintain and release desired tension on the suture, for example.

OVERVIEW

In Example 1, a suture instrument includes a handle and an instrument post extending from the handle, the handle including a cavity; a cover slidably attached to the handle to cover the cavity; a post extending upward from a bottom surface of the cavity; and a suture spool removably positioned over the post; wherein the post includes a force member configured to provide upward force on the spool to move the spool upward when the cover is slid off of the spool.

In Example 2, Example 1 can optionally include a second post extending upward from a bottom surface of the cavity and the spool including one or more engagement members that engage with the second post when the cover is slid over the cavity.

In an Example 3, Examples 1 or 2 can optionally include the cover including one or more projections projecting downward to apply force against a top of the spool when the cover is slid over the spool.

In an Example 4, Example 3 can optionally include wherein when the spool has downward force applied to the top of the spool, the spool is depressed farther down over the post.

In an Example 5, Example 4 can optionally include wherein the force member includes first and second tangs of the post and when the spool is pressed downward by the cover, the post is squeezed such that the first and second tangs move closer toward each other.

In an Example 6, Example of 5 can optionally include wherein when the one or more projections of the cover are moved off of the top of the spool, the first and second tangs bias outward to move the spool upward.

In Example 7, any of Examples 1-6 can optionally include the instrument post extending from the handle being hollow to receive a suture.

In Example 8, any of Examples 1-7 can optionally include wherein an outer diameter of the post matches an inner diameter of the suture spool.

In an Example 9, any of Example 1-8 can optionally include wherein the cover includes a projection on an outer surface to slide the cover back and forth over the spool.

In Example 10, any of Examples 1-9 can optionally include wherein the handle includes first and second grooves that mate with first and second projections on the cover.

Example 11 is a method including placing a spool over a post in a cavity of a handle of a suture instrument; sliding closed a cover on the handle; depressing the spool using force applied by the cover; and when depressed, the spool being biased upward by a force member of the post.

In Example 12, Example 11 can optionally include sliding open the cover on the handle.

In Example 13, Example 12 can optionally include wherein sliding open the cover removes the force on the top of the spool.

In Example 14, Example 13 can optionally include wherein the force member of post includes first and second tangs of the post, and wherein when the force is removed from the top of the spool, the first and second tangs bias outward to move the spool upward.

In Example 15, any of Examples 11-14 can optionally include wherein the handle includes a locking post extending upward from a bottom surface of the cavity and the spool includes one or more engagement members that engage with the locking post when the cover is slid over the cavity.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
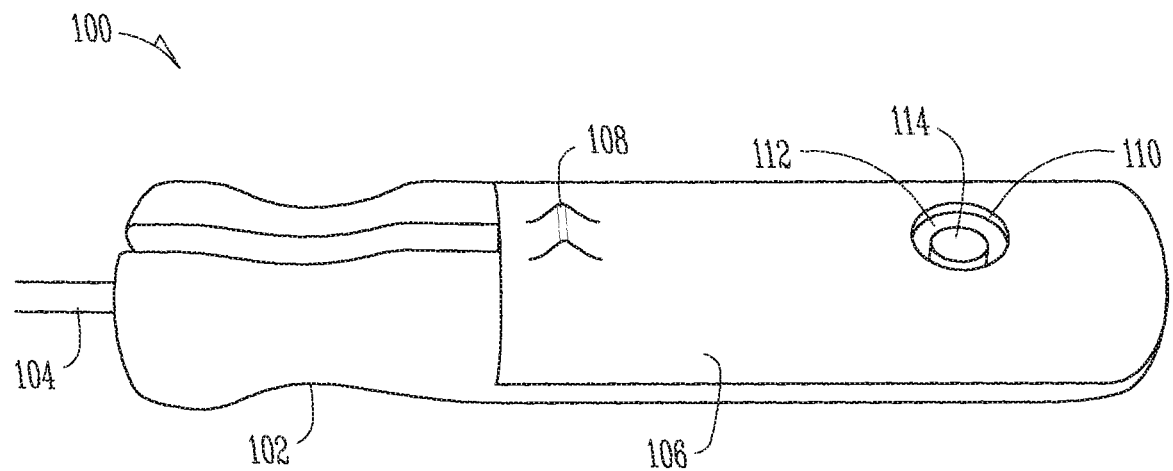
FIG. 1 shows perspective view of a suture instrument, in accordance with one embodiment.
Figure 2:
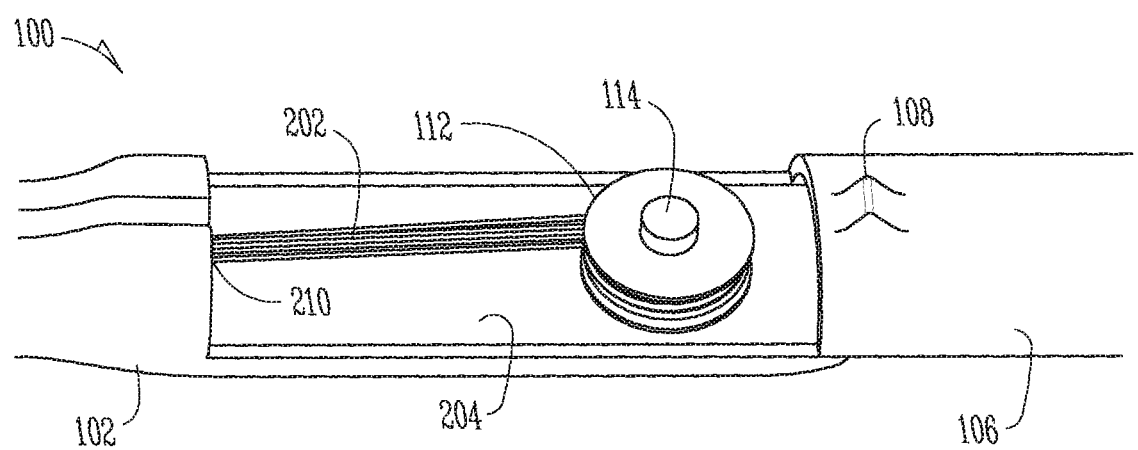
FIG. 2 shows another perspective view of the suture instrument of FIG. 1.

FIGS. 1 and 2 show perspective views of a suture instrument 100, in accordance with one embodiment.

Suture instrument 100 can generally include a handle 102 and an instrument post 104 extending from the handle 102. The handle can include a cavity 204 to hold a suture spool 112. The instrument post 104 can be hollow and can include an opening 210 within the cavity 204 to receive a suture 202 which can extend from the suture spool down post 104 to the working end of the instrument 100.

A cover 106 can be slidably attached to the handle 102 to cover the cavity 204. A projection 108 on a top surface of the cover 106 can allow for one-handed operation of the cover. By using a thumb, for example, the user can slide the cover 106 back and forth over the cavity 204. As will be further discussed this action, will tighten or release tension on the suture spool 112 and suture 202. A window 110 can be provided in the cover 106 over the spool 112 to allow for visual inspection while in use, for example.

A post 114 can extend upward from a bottom surface of the cavity 204 and receive the suture spool 112 when the suture spool 112 is place over the post 114. An outer diameter of the post 114 can generally match an inner diameter of the suture spool 112 such that the spool can rotate on the post 114. In one example post 114 can include a split post.

Figure 3:
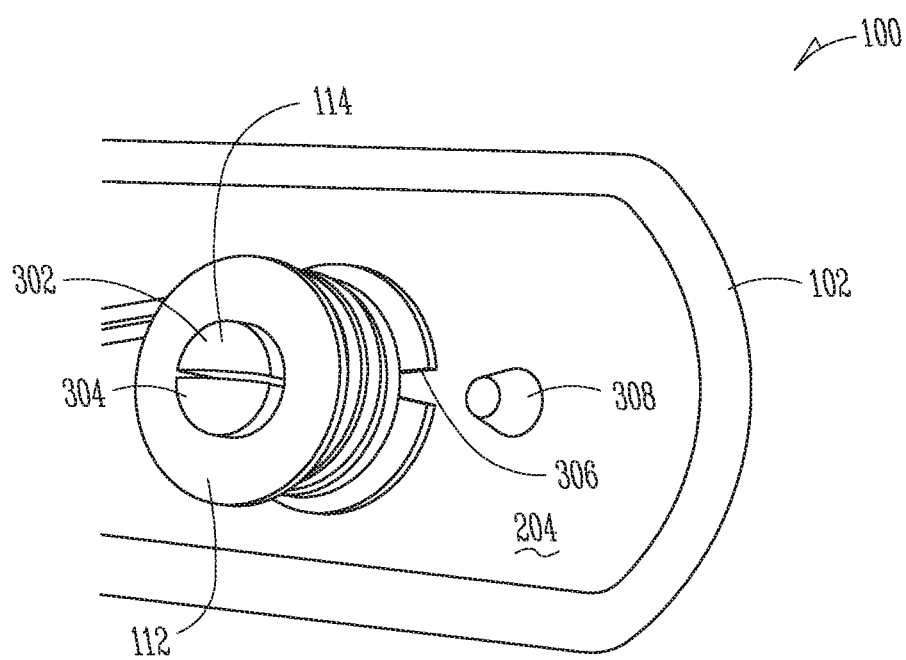
FIG. 3 shows a view of a detail of the suture instrument of FIG. 1

FIG. 3 shows a view within the cavity 204 of the suture instrument 100. A locking mechanism, such as a locking post 308 can be located on a bottom surface of the cavity 204 and extend upward. The spool 112 can include on or more engagement members, such as radial grooves 306 on a bottom surface of the spool 112. The post 308 is configured to engage the one or more grooves 306 when the spool 112 is pushed downward to lock the spool 112 in place to prevent rotation of the spool 112. As will be discussed below, this can occur when the cover 106 is in the closed position of FIG. 1.

The post 114 can include a force member configured to provide upward force on the spool 112 when the cover is slid off of the spool 112. In one option the force member can be first and second tangs 302, 304 as parts of a split post. The first and second tangs 302, 304 can bias outward away from each other. Thus, if no force is applied to keep the spool 112 down over the post 114, the outward bias of tangs 302, 304 causes the spool 112 to lift upwards and releases the spool 112 from the post 308, thus allowing the spool 112 to freely rotate.

Figure 4:
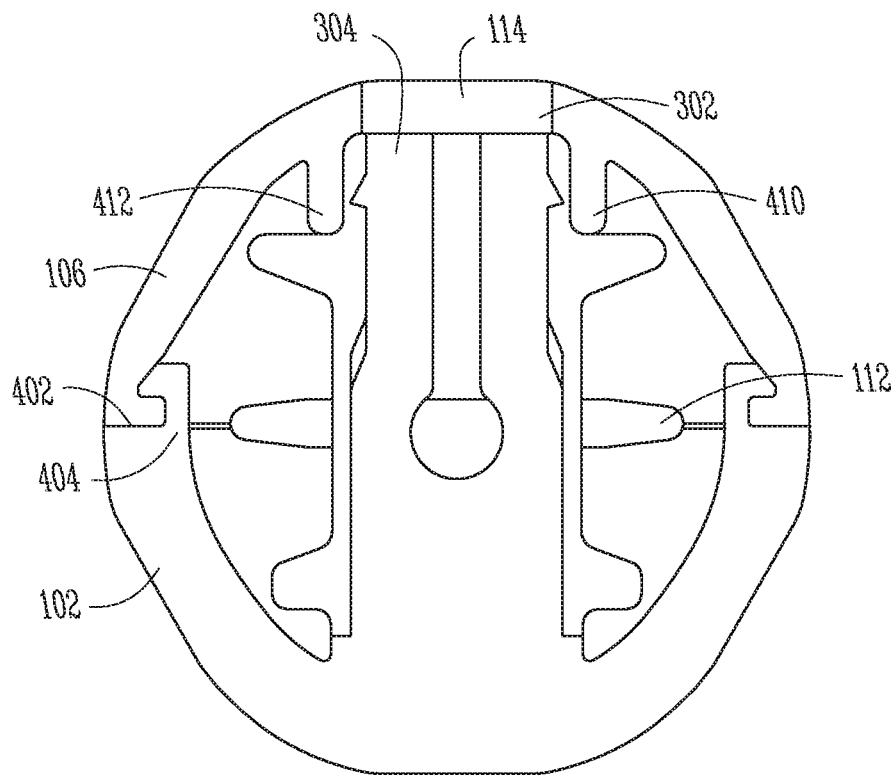
FIG. 4 shows a cross-section view of a handle of the surgical instrument, in accordance with one embodiment.

FIG. 4 shows a cross-section view of a handle 106 of the surgical instrument 100, in accordance with one embodiment. The cover can include one or more projections, such as tapered fins 410, 412 projecting downward to apply force against a top of the spool 112 when the cover 106 is slid over the spool 112. This depresses the spool 112 farther down over the post 114 until the spool engages the post 308 (FIG. 3), thus locking the spool 112 from rotating. When the spool 112 is pressed downward by the fins 410, 412 of the cover 106, the post 114 can be squeezed such that the first and second tangs 302, 304 move closer toward each other. The potential energy formed by squeezing the tangs 302, 304 together acts as a spring, so to speak, providing the upward force necessary to release the spool 112 off the post 308 when the one or more fins 410, 412 of the cover 106 are moved off of the top of the spool 112. Thus first and second tangs 302, 304 can bias outward to move or urge the spool 112 upward.

The cover 106 further can include projection 402 on each side which can be slidably received within grooves 404 on the handle 102.

In use, the spool 112 can be placed over the post 114 and the user extends any amount of suture needed. The user can then slide the cover 106 so that fins 410, 412 force the spool 112 down over the post 308, locking everything in place. As noted, pushing down the spool 112 also squeezes together tangs 302, 304. Thus, the spool 112 is being biased upward by the potential energy of squeezed tangs 302, 304. However, the cover 106 holds the spool 112 down in a locked position.

When the user needs to release the suture, the cover 106 can be slid open. This releases the force on the spool 112 and the tangs 302, 304 of the post 114 bias apart to push the spool 112 upward so that the spool 112 can be released from the locking mechanism. The spool 112 can then freely rotate to allow the user to extend more suture off the spool 112.

Among other advantages, the present system allows for a user to manage long lengths of suture without entanglement since it is easy to lock and unlock the device with a single hand. Also, the system helps to maintain tension on a suture when linked to an implant on the end of an insertion device. The present system also creates a one handed solution in releasing a relatively large number of long sutures from the instrument handle.

The present system can used with any suture instrument and basically any application where there are free suture tails that need proper management.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. An apparatus comprising:
    a suture instrument including a handle and an instrument shaft extending from the handle, the handle including a cavity;
    a cover slidably attached to the handle to cover the cavity;
    a post attached to and extending upward from a bottom surface of the cavity; and
    a suture spool removably positioned over the post;
    wherein the post includes a force member configured to provide upward force on the spool to move the spool upward away from the bottom surface of the cavity when the cover is slid off of the spool.

2. The apparatus of claim 1, wherein the handle includes a second post extending upward from a bottom surface of the cavity and the spool includes one or more engagement members that engage with the second post when the cover is slid over the cavity.

3. The apparatus claim 1, wherein the cover includes one or more projections projecting downward to apply force against a top of the spool when the cover is slid over the spool.

4. The apparatus of claim 3, wherein when the spool has downward force applied to the top of the spool, the spool is depressed farther down over the post.

5. The apparatus of claim 1, wherein the instrument shaft extending from the handle is hollow to receive a suture.

6. The apparatus of claim 1, wherein an outer diameter of the post matches an inner diameter of the suture spool.

7. The apparatus of claim 1, wherein the cover includes a projection on an outer surface to slide the cover back and forth over the spool.

8. The apparatus of claim 1, wherein the handle includes first and second grooves that mate with first and second projections on the cover.

9. An apparatus comprising:
a suture instrument including a handle and an instrument shaft extending from the handle, the handle including a cavity;
a cover slidably attached to the handle to cover the cavity;
a post extending upward from a bottom surface of the cavity; and
a suture spool removably positioned over the post;
wherein the post includes a force member configured to provide upward force on the spool to move the spool upward when the cover is slid off of the spool; wherein the cover includes one or more projections projecting downward to apply force against a top of the spool when the cover is slid over the spool, wherein when the spool has downward force applied to the top of the spool, the spool is depressed farther down over the post, and wherein the force member includes first and second tangs of the post and when the spool is pressed downward by the cover, the post is squeezed such that the first and second tangs move closer toward each other.

10. The apparatus of claim 9, wherein when the one or more projections of the cover are moved off of the top of the spool, the first and second tangs bias outward to move the spool upward.

11. A method comprising:
placing a spool over a post in a cavity of a handle of a suture instrument wherein the post is attached to and extends upward from a bottom surface of the cavity;
sliding closed a cover on the handle;
depressing the spool using force applied by the cover; and
when depressed, the spool being biased upward by a force member of the post, wherein the post includes a force member configured to provide upward force on the spool to move the spool upward away from the bottom surface of the cavity when the cover is slid off of the spool.

12. The method of claim 11, further comprising sliding open the cover on the handle.

13. The method of claim 12, wherein sliding open the cover removes the force on the top of the spool.

14. A method comprising:
placing a spool over a post in a cavity of a handle of a suture instrument;
sliding closed a cover on the handle;
depressing the spool using force applied by the cover;
when depressed, the spool being biased upward by a force member of the post; and
sliding open the cover on the handle, wherein sliding open the cover removes the force on the top of the spool, and wherein the force member of the post includes first and second tangs of the post, and wherein when the force is removed from the top of the spool, the first and second tangs bias outward to move the spool upward.

15. The method of claim 14, wherein the handle includes a locking post extending upward from a bottom surface of the cavity and the spool includes one or more engagement members that engage with the locking post when the cover is slid over the cavity.

* * * * *

UNITED STATES PATENT AND TRADEMARK OFFICE
CERTIFICATE OF CORRECTION

PATENT NO. : 10,603,032 B2
APPLICATION NO. : 15/566490
DATED : March 31, 2020
INVENTOR(S) : Walters et al.

Page 1 of 1

It is certified that error appears in the above-identified patent and that said Letters Patent is hereby corrected as shown below:

On the Title Page

On page 2, in Column 1, under "Other Publications", Lines 5-6, delete "Comunication Persuant" and insert --Communication Pursuant-- therefor In the Claims In Column 6, Line 10, in Claim 11, after "instrument", insert --,--

Signed and Sealed this
Fourteenth Day of July, 2020

Andrei Iancu
*Director of the United States Patent and Trademark Office*